United States Patent [19]

Favaron

[11] Patent Number: 4,549,544
[45] Date of Patent: Oct. 29, 1985

[54] CLIP STOP FOR A SURGICAL LIGATING INSTRUMENT

[75] Inventor: James A. Favaron, Amelia, Ohio

[73] Assignee: Senmed, Inc., Cincinnati, Ohio

[21] Appl. No.: 546,928

[22] Filed: Oct. 31, 1983

[51] Int. Cl.$^4$ .................... A61B 17/08; B65H 25/26
[52] U.S. Cl. ................................. 128/335; 227/19; 227/DIG. 1
[58] Field of Search ............... 128/325, 326, 346, 321; 227/19, 119, DIG. 1, 43, 132, 149; 29/243.56

[56] References Cited

U.S. PATENT DOCUMENTS

| | | | |
|---|---|---|---|
| 3,270,745 | 9/1966 | Wood | 128/325 |
| 3,463,156 | 8/1969 | McDermott | 128/325 |
| 3,631,707 | 1/1972 | Miller | 128/325 |
| 3,844,289 | 10/1974 | Noiles | 128/334 |
| 4,152,920 | 5/1979 | Green | 72/410 |
| 4,242,902 | 1/1981 | Green | 72/410 |
| 4,296,751 | 10/1981 | Blake, III et al. | 128/325 |
| 4,325,376 | 4/1982 | Klieman et al. | 128/325 |

*Primary Examiner*—Gene Mancene
*Assistant Examiner*—C. W. Shedd
*Attorney, Agent, or Firm*—Frost & Jacobs

[57] ABSTRACT

An improved clip pusher and stop system for a surgical ligator of the type having first and second clip-clamping jaws, a pair of handles to actuate the jaws, a magazine of ligating clips, a pusher track extending to the forward ends of the jaws, a pusher to transfer a clip along the pusher track from the magazine to a forward position between the jaws, and a stop to prevent rearward movement of the clip in the pusher track during the clip-applying and clamping procedure. The improved stop comprises a substantially L-shaped resilient member having a long leg and a short leg. The long stop leg lies along a depression in the first jaw and is affixed near its free end to the first jaw. The short leg extends between the first and second jaws and is receivable in a perforation in the second jaw when the jaws are actuated to clamp a clip. The short leg has an intermediate clip-contacting portion normally extending across the pusher track. The clip-contacting portion is shiftable by an advancing clip out of the pusher track, and returns into the pusher track behind a fully advanced clip to prevent rearward movement of the clip during the clip-applying and clamping procedure and to dislodge the clip from the pusher if adhered thereto by body fluids or the like.

17 Claims, 13 Drawing Figures

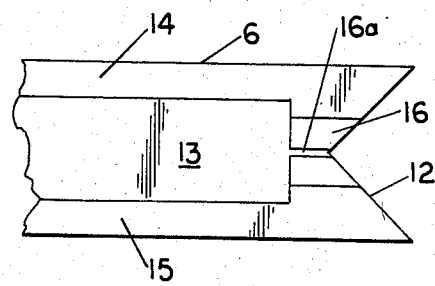
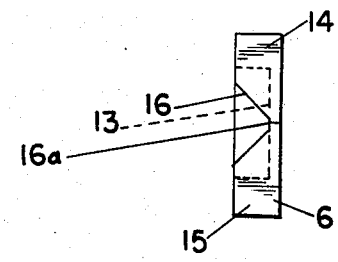
FIG. 4    FIG. 5
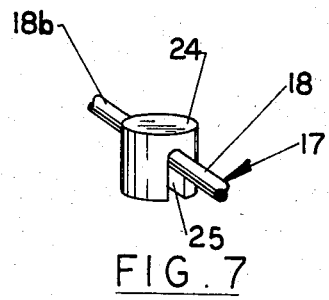
FIG. 7
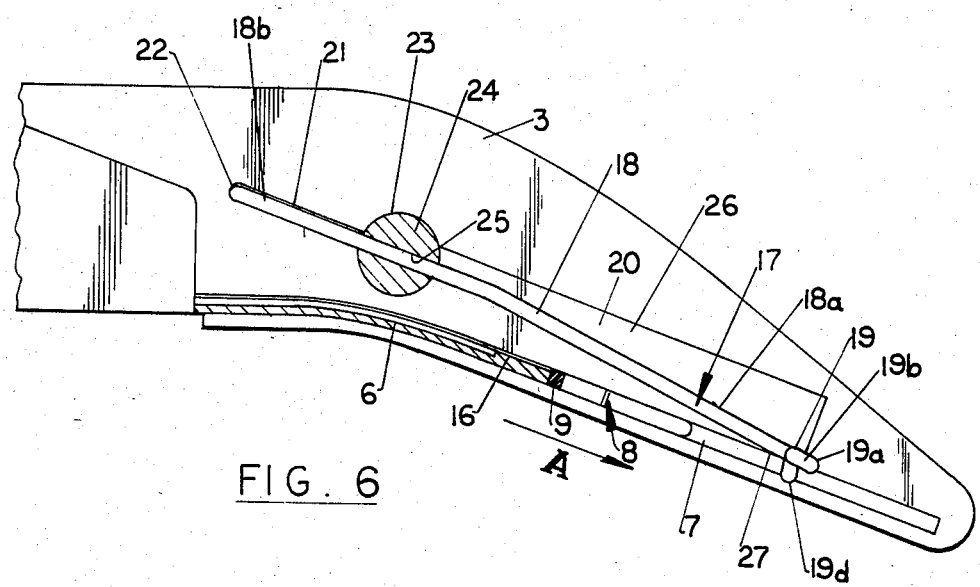
FIG. 6

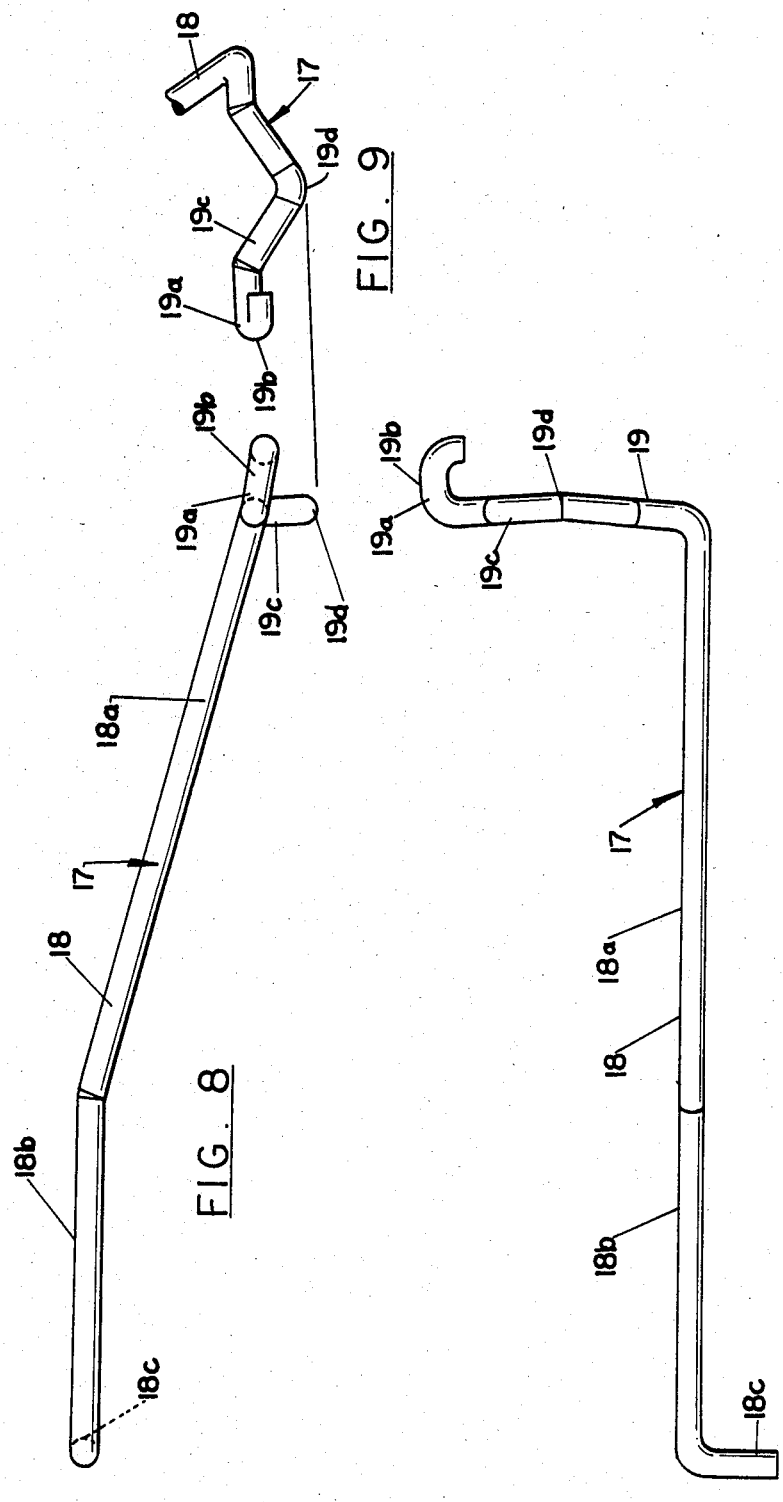

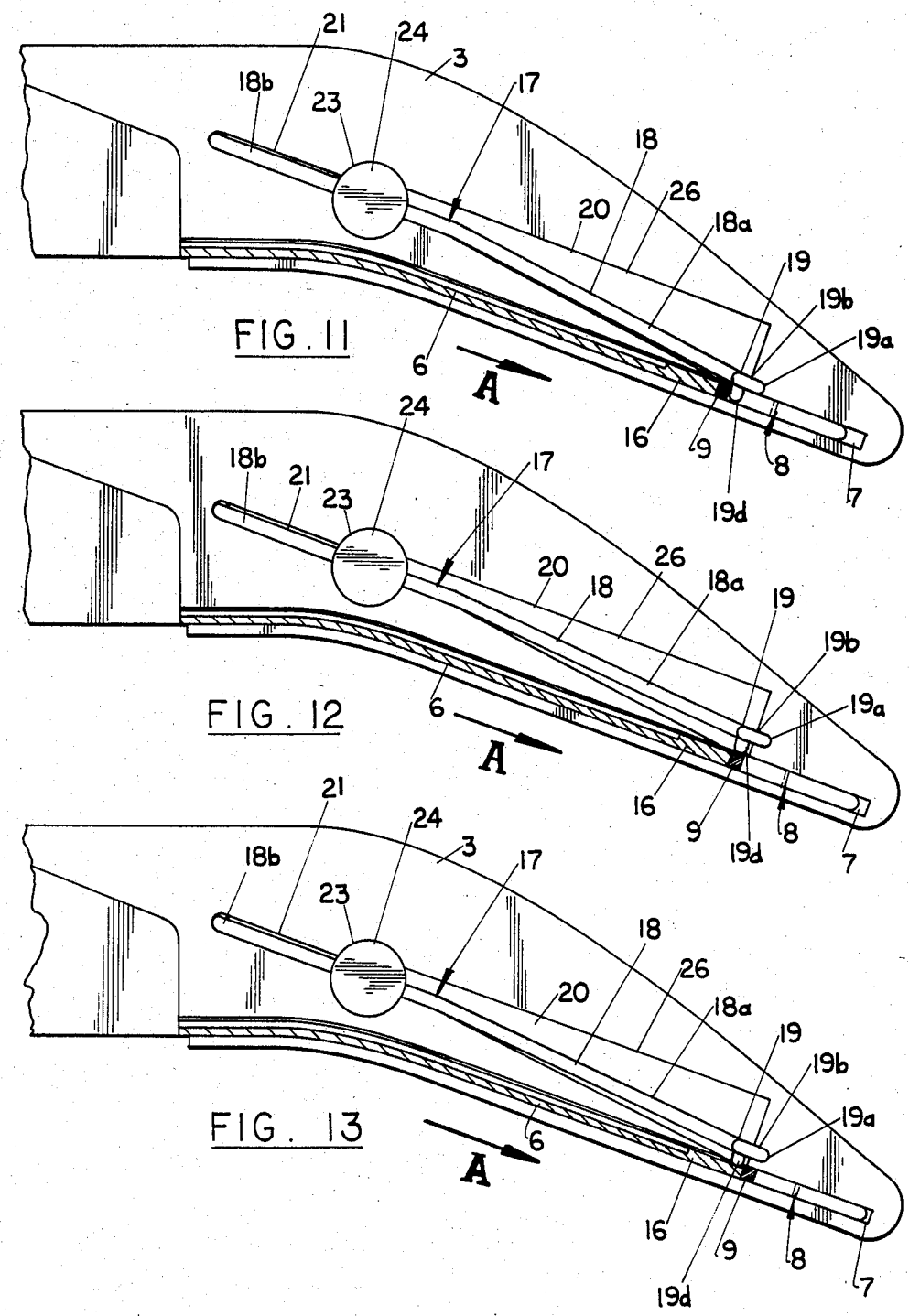

CLIP STOP FOR A SURGICAL LIGATING INSTRUMENT

REFERENCE TO RELATED APPLICATION

The present invention relates to improvements in surgical ligating instruments of the general type taught in co-pending application Ser. No. 435,380, filed Oct. 20, 1982, in the names of Robert G. Rothfuss, David K. Kuhl, Federico Bilotti, Hugh Melling and Earl J. Mills, and entitled: LIGATOR

TECHNICAL FIELD

The invention relates to improvements in a surgical ligator for applying clamping clips to veins, arteries, blood vessels and other body tissues, and more particularly to an improved clip stop therefor, which prevents rearward movement of a clip located between the ligator jaws during the clip applying and clamping procedure, and which will separate the clip from the pusher if adhered thereto by body fluids or the like.

BACKGROUND ART

Recently, there has been an increasing number of surgeons using clips, in lieu of conventional suture ties, to occlude blood vessels and the like. In a typical surgical procedure, many veins, arteries and blood vessels must be tied off, prior to the severing thereof, in order to reach the surgical site. This is an often difficult and time-consuming procedure, since many vessels are located in areas where there is little room to work. It is important that the occlusion be positive to minimize bleeding and, due to the fact that once severed, the blood-carrying vessels tend to retract into surrounding tissue and are difficult to retrieve. As used herein and in the claims, the terms "vessel" and "vessels" should be considered in the broad sense to be inclusive of veins, arteries and the like, to which ligator clips are normally applied.

Prior art workers have devised numerous types of surgical ligating instruments designed to clamp blood vessels. There are, for example, reusable, permanent-type ligating instruments, and instruments which are intended to be disposed of after use. There are also ligating instruments wherein each clip is individually loaded in the instrument. Other ligating instruments utilize pre-sterilized cartridges holding a multiplicity of clips. Yet another general class of ligating instruments is provided with a magazine within the instrument containing a plurality of clips.

The teachings of the present invention are applicable to ligating instruments of the general type having a pair of clamping jaws and a pusher by which a clip is located in position between the jaws, ready to be clamped about a blood vessel or the like. While not intended to be so limited, for purposes of an exemplary showing, the teachings of the present invention will be described in their application to a disposable surgical ligator of the type taught in the above mentioned co-pending application Ser. No. 435,380. The teachings of this co-pending application are incorporated herein by reference.

Briefly, the disposable ligator of the co-pending application comprises a first handle terminating at its forward end in a first jaw. A second jaw is pivotally mounted to the first handle so as to cooperate with the first jaw. A second handle is pivotally mounted at its forward end to the first handle and is provided with a lug to actuate the second jaw. The handles are shiftable between open and closed positions, and shift the first and second jaws between open and closed, clip-clamping positions.

A clip tube or magazine, containing a plurality of clips lying one behind the other in the same plane, is mounted in the first handle. A feeder shoe is mounted in the clip tube and constantly urges the row of clips forwardly therein through the agency of a constant-force coil spring. Adjacent and along the clip tube, a pusher is mounted in the first handle in a pusher track which is continued to the forward ends of the jaws. The pusher is shiftable by the first and second handles between a retracted position when the handles are closed and an extended position to locate a clip in the pusher track between the forward ends of the jaws when the handles are open. The first handle provides a ramp structure leading to the pusher track at the forward end of the clip tube. The ramp structure is covered by the pusher when in its extended position. The ramp is exposed by the pusher when in its retracted position, enabling the forwardmost clip of the row to be transferred from the clip tube, via the ramp, to the pusher track in front of the pusher, due to the forward urging of the clips by the feeder shoe.

When the first and second handles are shifted from their closed to the open positions, the first and second jaws will also shift from their closed to the open positions and the pusher will locate a clip in the pusher track at a position between the forward ends of the jaws, ready for clamping. When the first and second handles are squeezed toward each other, the pusher will shift to its retracted position enabling the next forwardmost clip of the row to be ramped or transferred into the pusher track. Immediately thereafter, the first and second jaws will close, clamping the clip therebetween about the vessel to be occluded. This sequence of events is repeated with each opening and closing of the handles, the clip feeding system requiring no force on the part of the surgeon to accomplish its purpose.

In the use of a ligator of this general type, two problems are encountered. First of all, when the jaws, with a clip located therebetween, are caused to approach a vessel to be ligated, and when the vessel is located between the clip legs, any further advance of the jaws in the clip applying direction may cause the vessel to shift the clip rearwardly in the pusher track and out of its proper position for clamping between the jaws.

The above noted co-pending application teaches a solution of this problem comprising the provision of an integral pin mounted on the first jaw alongside the pusher track and extending toward the second jaw. The free end of the pin is receivable in a perforation in the second jaw when the jaws are closed to clamp a clip. The pin acts as a stop, limiting the depth to which the vessel to be ligated can enter between the jaws. Since the vessel abuts the pin, the vessel cannot shove the clip rearwardly beyond the pin.

U.S. Pat. No. 4,242,902 teaches a clip stop preventing rearward movement or displacement of the clip in the jaws of a ligating instrument. In the primary embodiment of this patent, a resilient arm-like member is provided having a free end which enters between the jaws and behind the clip. As the jaws are closed to clamp the clip, the free end of the stop is so configured as to be cammed out from between the jaws, by the jaws themselves.

The second problem frequently encountered in the use of the general type of ligator contemplated is the result of the accumulation of blood and/or other body fluids on the end of the pusher, rendering the pusher end tacky. Since, in the type of ligating instrument described above, the pusher retracts from between the jaws during the initial stages of the clip applying and clamping process, the clip sometimes tends to adhere to the pusher end and is retracted with the pusher end from between the jaws. The above noted U.S. Pat. No. 4,242,902 does not address this problem because the ligator taught therein does not have a pusher of the type contemplated. The stop pin described with respect to the above noted co-pending application does not solve this problem since it lies to the side of the pusher track and does not contact or engage the clip at any time.

The present invention contemplates a stop for a surgical ligating instrument wherein the stop prevents the clip from being shoved rearwardly in the pusher track during application and clamping thereof. Furthermore, the stop assures that the clip is separated from the pusher during the initial part of the clip-applying and clamping operation, when the pusher begins to retract from between the jaws. The stop itself is a simple structure made of resilient wire and remains between the jaws at all times.

DISCLOSURE OF THE INVENTION

According to the invention, there is provided an improved clip stop for a surgical ligator. The ligator is of the type having first and second clip-clamping jaws, a pair of handles to actuate the jaws, a magazine of ligating clips, a pusher track extending to the forward ends of the jaws, a pusher for transferring a clip along the pusher track from the magazine to a forward position between the jaws, and a stop to prevent rearward movement of the clip in the pusher track during the clip-applying and clamping procedure.

The improved stop comprises an elongated member of resilient wire having a substantially L-shaped configuration with a long leg and a short leg. The long leg is located in a depression in the first jaw. The free end of the long leg is bent at a right angle to the remainder of the long leg and extends into a perforation in the first jaw so as to maintain the proper orientation of the stop with respect to the first and second jaws. The long leg is affixed to the first jaw by means of a slotted plug-like fastener located near the free end of the long leg.

The short leg of the stop is angularly related to the long leg and extends between the first and second jaws. The free end of the short leg is receivable in a perforation in the second jaw so that the jaws can be closed, with the short leg of the stop remaining therebetween. The short leg has an intermediate clip-contacting portion configured in a V-shape and extending laterally of the short leg. The clip-contacting portion of the short leg normally extends across the pusher track, such that it normally lies within the path of travel of the pusher and a clip.

The long leg of the stop is so configured that the clip-contacting portion of the short leg normally extends across the pusher track. When the pusher advances a clip from the magazine toward the ends of the jaws, the base portion of the clip will abut the clip-contacting portion of the stop. Since the stop is made of resilient wire, the base portion of the clip will cam the clip-contacting portion of the stop out of its way and out of the pusher track. As soon as the base portion of the clip passes the clip-contacting portion of the stop, the clip-contacting portion of the stop will return partway to its normal position across the pusher track. Thus, the clip-contacting portion of the stop is located directly behind the clip base portion. When the clip is located on the vessel to be clamped, the stop will prevent the clip from being shoved rearwardly of the jaws by the vessel. During the initial stages of the clip-applying and clamping procedure, when the pusher begins to retract, the clip-contacting portion of the stop will ensure that the clip separates from the forward end of the pusher and is not carried rearwardly of the jaws by the pusher. When the clip has been fully applied to the vessel, the surgeon will allow the ligator instrument handles to return to their normal open position, simultaneously opening the jaws. At the same time, a new clip from the magazine will be located at the forward ends of the jaws by the pusher in the manner described above.

BRIEF DESCRIPTION OF THE DRAWINGS

FIG. 4 is a fragmentary, enlarged view of the free, pushing end of one embodiment of the pusher.

FIG. 5 is an end elevational view of the free end of the pusher of FIG. 4.

FIG. 6 is a fragmentary, elevational view, partly in cross-section, of the first jaw of the instrument of FIG. 1, illustrating the stop, the pusher track, the pusher and a clip.

FIG. 7 is a fragmentary prespective view of the plug of the present invention.

FIGS. 8, 9 and 10 are, respectively, a plan view, an end view and an elevational view of the stop of the present invention.

FIGS. 11 through 13 are fragmentary, elevational views, partly in cross-section, of the first jaw and illustrate in positions of a clip, the pusher and the stop in sequence during the location of a clip in position for clamping.

DETAILED DESCRIPTION OF THE INVENTION

Figure 1:
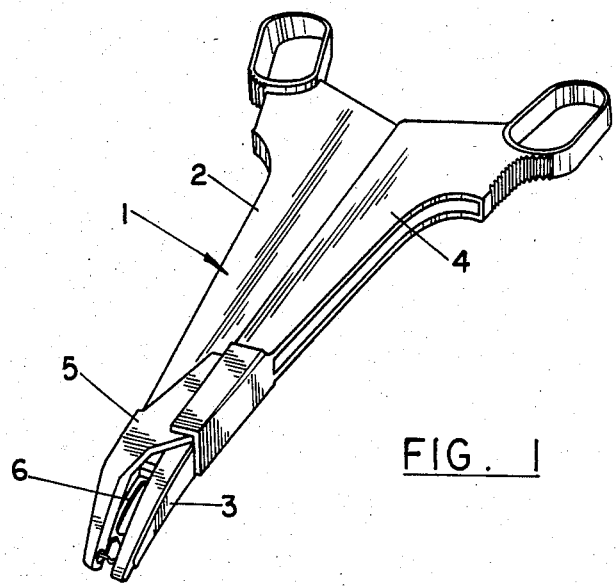
FIG. 1 is a perspective view of an exemplary surgical ligating instrument.

Reference is first made to FIG. 1 wherein an exemplary surgical ligating instrument is shown, of the type set forth in the above noted co-pending application. The ligator is generally indicated at 1, having a first handle 2 terminating in a first jaw 3 at its forward end. The ligator 1 has a second handle 4 and a second jaw 5. The jaw 5 and the forward end of second handle 4 are pivotally attached to the first handle 2, in such a way that the second jaw 5 is actuated by the second handle 4.

The internal components of the instrument 1 (not shown) do not constitute a limitation of the present invention. For a better understanding of the invention, suffice it to say that the handle 2 contains an elongated tube or magazine having a plurality of clips, lying one behind the other in the same plane and a spring biased feeder shoe to constantly urge the row of clips forwardly in the magazine. Adjacent and along the clip tube, a pusher is mounted in handle 2 in a pusher track which is continued to the forward ends of the jaws. In FIG. 1, the pusher is shown at 6.

Reference is briefly made to FIG. 6 which shows that surface of jaw 3 which opposes jaw 5. Jaw 3 is provided with a longitudinally extending slot or groove 7 in which the pusher 6 rides. The groove 7 constitutes a continuation of the pusher track within handle 2. It will be understood that the jaw 5 has a corresponding slot (not shown) which also constitutes a continuation of the pusher track, and when the jaws are in their open position, the pusher 6 can be shifted in the slot 7 in jaw 3 and the corresponding slot (not shown) in jaw 5, to locate a clip in the pusher track at the forward end of the jaws.

Handle 2 provides a ramp structure (not shown) at the forward end of the clip tube or magazine, which ramp structure is covered by the pusher when in its extended position. The ramp is exposed by the pusher in its retracted position, enabling the forwardmost clip in the magazine to be transferred from the magazine, via the ramp, to the pusher track in front of the pusher.

Figure 3:
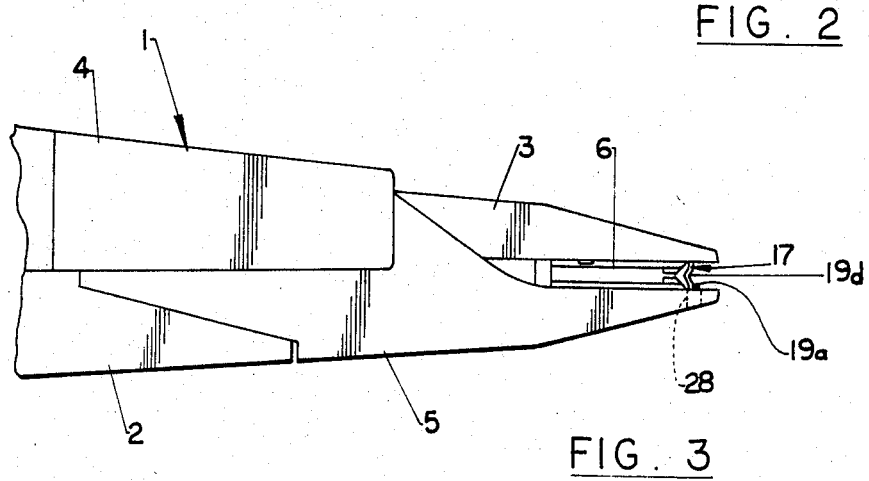
FIG. 3 is a fragmentary, elevational view of the jaws of the ligating instrument of FIG. 1.

In the instrument 1 of FIG. 1, the parts are so arranged that when handles 2 and 4 are in their open position as shown, and jaws 3 and 5 are also in their open position, and the pusher 6 will be in its forwardmost or extended position. When the handles 2 and 4 are shifted toward each other to their closed position, closing jaws 3 and 5, the pusher will be withdrawn to its retracted position. Thus, in use, when the instrument 1 is initially handed to the surgeon, it will be as illustrated in FIG. 1 without a clip located at the forward ends of jaws 3 and 5. It is only necessary for the surgeon to squeeze handles 2 and 4 together and close jaws 3 and 5, causing the pusher 6 to achieve its retracted position. When the handles 2 and 4 are released and the jaws 3 and 5 are open, the pusher 6 will provide a first clip at the forward ends of the jaws. The surgeon then applies this clip to a vessel to be ligated, squeezing handles 2 and 4 together and closing jaws 3 and 5 to clamp the clip about the vessel. Simultaneously, the pusher 6 will have been withdrawn to its retracted position to pick up the next clip. Upon release of the handles 2 and 4 and the opening of jaws 3 and 5, the next clip will be presented by the pusher 6 to the forward ends of the jaws 3 and 5, ready to apply to the vessel. FIG. 3 is an enlarged view of the jaws 3 and 5, and illustrates them in their initial condition as the instrument is first handed to the surgeon, with the pusher 6 in its forward or extended position without a clip.

Figure 2:
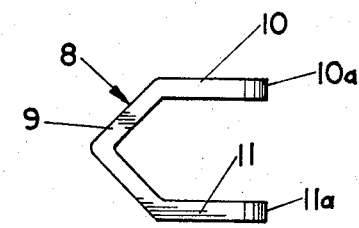
FIG. 2 is an elevational view of an exemplary ligating clip.

An exemplary clip is illustrated in FIG. 2. The clip is preferably made of an appropriate metal suitable for use in the body of a patient and in a surgical environment. The clip is generally indicated at 8, having a V-shaped base portion 9 terminating at either end in legs 10 and 11. The free ends 10a and 11a of legs 10 and 11 may be rounded as shown. The inside facing surfaces (not shown) of legs 10 and 11 may be grooved or knurled to assure a positive engagement of the vessel to be ligated.

The forwardmost end of one embodiment of pusher 6 is illustrated in FIGS. 4 and 5. As is most clearly seen in FIG. 4, the forwardmost edge of the pusher 6 is configured as a V-shaped notch 12 corresponding in shape to the base portion 9 of clip 8. This enables the forward end of pusher 6 to engage the base portion 9 of the clip 8 and move it forwardly to the forward ends of jaws 3 and 5.

The pusher 6 is made of resilient material appropriate for use in a surgical environment (preferably plastic), and has a thin central body portion 13 with edge portions 14 and 15 of greater thickness. Thus, as can best be seen in FIG. 5, the pusher 6 has a channel-shaped configuration. In its preferred form, the forwardmost end of pusher 6 is of the same thickness as edge portions 14 and 15. However, a longitudinal V-shaped notch 16 may be formed therein, extending from notch 12 to the central body portion 13, and having a base portion 16a substantially co-planar with the inside surface of the central body portion 13. The presence of longitudinal notch 16 is not necessary in the present invention; it is merely illustrative of one embodiment of the invention which may be used when the thickness of the body of pusher 6 is greater than the thickness of clip 8. It is not intended to limit the scope of the invention.

Reference is now made to FIGS. 8, 9 and 10, wherein the stop of the present invention is illustrated. Like parts have been given like index numerals and the stop is generally indicated at 17.

As is most clearly determined from FIG. 10, the stop comprises a substantially L-shaped member of resilient wire, having a long leg 18 and a short leg 19. Any appropriate resilient wire material suitable for use in a surgical environment may be used to fabricate the stop 17. Excellent results have been achieved, for example, through the use of stainless steel wire.

The long leg 18 is made up of two angularly related portions 18a and 18b. At its free end, the leg 18 terminates in a laterally extending portion 18c forming an angle of about 90° with the leg portion 18b.

The short leg 19 lies in an angle of substantially 90° to the long leg 18 and terminates at its free end in a hook-shaped portion 19a adapted to present an arcuate or rounded end 19b, the purpose of which will be described hereinafter. The short leg 19 has an intermediate V-shaped portion 19c, the apex 19d of which constitutes a clip-engaging nose, as will be apparent hereinafter.

Reference is now made to FIG. 6, wherein the stop 17 is shown mounted on jaw 3. To this end, that surface of jaw 3 which faces the corresponding surface of jaw 5 is provided with a substantially longitudinally extending depression 20. The depression 20 has a first rectilinear portion 21 near the rearward end of jaw 3 and terminating in a perforation 22. The rectilinear portion 21 is adapted to receive the portion 18b of the long leg 18 of stop 17. The perforation 22 receives free end 18c of long leg 18. The rectilinear portion 21 of depression 20 intersects a circular perforation 23. It will be noted from FIG. 6 that the perforation 23 is spanned by the long leg portion 18b. The perforation 23 is adapted to receive a slotted plug 24.

The slotted plug 24 is illustrated in FIG. 7. The plug 24 is of cylindrical configuration having a longitudinal slot 25 formed therein. The slot 25 is so sized as to just nicely receive the portion 18b of the long leg 18 of stop 17.

As will be clear from FIG. 6, the plug 24 maintains the stop 17 in position in the elongated depression 20 of jaw 3. When inserted in perforation 23, the plug may be adhered therein by adhesive means, ultrasonic welding or the like. It will further be evident that the engagement of the free end 18c of the stop long leg 18 in perforation 22 will prevent the stop 17 from rotating within slotted plug 24 and will ensure that the short leg 19 of stop 17 will extend upright (as view in FIG. 6) toward jaw 5, as shown in FIGS. 1 and 3.

That portion 26 of longitudinal depression 20, located forwardly of circular opening 23, is of wedge-shaped configuration, as shown in FIG. 6, widening as it extends away from the circular opening 23 and toward the forward end of jaw 3. At its forwardmost end, the portion 26 of depression 20 lies adjacent pusher track 7. The depression 20 is deeper than the pusher track 7 forming a shoulder therebetween at 27.

The portion 26 of depression 20 is of such length as to accommodate portion 18a of the stop long leg 18. The angular relationship between the portions 18a and 18b of long leg 18 is such that the end of long leg portion 18a which is adjacet short leg 19 normally abuts the shoulder 27 formed between the pusher track 7 and the portion 26 of depression 20. When the stop 17 is in this normal position, it will be noted from FIG. 6 that the clip-contacting nose 19d of short leg 19 extends across pusher track 7.

The stop 17, having been described in detail, the operation of these elements will now be described. As indicated above, when the surgeon initially receives the ligating instrument 1, it will be in the condition illustrated in FIG. 1, with the handles 2 and 4 normally in their open positions and the first and second jaws 3 and 5 also in their normally open positions. The pusher 6 will be in its extended position, and there will be no clip located between the jaws. The surgeon will shift handles 2 and 4 to their closed positions, closing jaws 3 and 5. This action shifts the pusher 6 from its extended position to its retracted position, enabling a clip 8 to be transferred from the clip tube or magazine into the pusher track 7. When the surgeon allows handles 2 and 4 and jaws 3 and 5 to return to their normal, open positions, the pusher 6 will again return to its extended position, locating the clip 8 at the forward ends of the jaws 3 and 5 in the pusher track 7. When this first clip is applied and clamped on a vessel to be ligated, shifting of handles 2 and 4 and jaws 3 and 5 to their closed positions will again cause the pusher 6 to return to its retracted position, and the next clip will be transferred from the clip tube or magazine to the pusher track 7. Upon completion of the clip clamping operation, when handles 2 and 4 and jaws 3 and 5 are again permitted to return to their normal open positions, the pusher 6 will locate the next clip 8 at the forward ends of jaws 3 and 5, ready to be applied and clamped. This overall procedure can be repeated until the supply of clips is exhausted. When this happens, the instrument 1 may be provided with means to lock handles 2 and 4 and jaws 3 and 5, giving the surgeon an immediate indication that the instrument magazine is empty.

FIGS. 6, 11, 12 and 13 illustrate in sequence the operation of the pusher 6 and the stop 17 when the instrument handles 2 and 4 and the instrument jaws 3 and 5 shift to their normal, open positions. In FIG. 6, the pusher 6 is illustrated as advancing a clip 8 in pusher track 7 in the direction of arrow A toward the forwardmost end of jaw 3. As indicated above, the pusher 6 and clip 8 are simultaneously advancing in a corresponding pusher track in jaw 5 (not shown in FIGS. 6, 11, 12 and 13). The clip contacting nose 19d of stop 17 is in its normal position extending across the pusher track 7.

As is illustrated in FIG. 11, a further advance of pusher 6 and clip 8 in the direction of arrow A will bring the V-shaped base 9 of clip 8 into contact with the nose 19d of stop 17.

The V-shaped configuration of the stop nose 19d and the V-shaped configuration of base 9 of clip 8 will cooperate, such that when the clip 8 and pusher 6 advance further in the direction of arrow A, the stop nose 19d will be cammed out of pusher track 7, as shown in FIG. 12. This is made possible by the fact that the portion 18a of long leg 18 of stop 17 can shift in the portion 26 of depression 20 of jaw 3.

As soon as the base portion 9 of clip 8 passes beyond the stop nose 19d, the nose 19d will return partway to its normal position and to a position behind the base portion 9 of clip 8, as shown in FIG. 13. The pusher 6 can shift the clip 8 to a forward position very near the end of pusher track 7. At this point, the clip 8 is ready to be applied and clamped to a vessel to be ligated.

When the clip 8 is applied to a vessel (not shown), the vessel will extend between the legs 10 and 11 of the clip 8 and will contact the base portion 9 thereof. Slight forward movement of the instrument jaws 3 and 5 will cause the vessel to tend to push rearwardly against the clip base portion 9 and the pusher 6, possibly shifting the clip 8 rearwardly (i.e. in a direction opposite arrow A in FIG. 13) in the pusher track 7 as handles 2 and 4 are squeezed together to clamp clip 8 on the vessel. In the absence of stop 17, the clip 8 and pusher 6 could move rearwardly in pusher track 7 to an extent that the clip 8 was no longer in proper position to be clamped. However, since the nose 19d of stop 17 is located behind the clip base portion 9, as shown in FIG. 13, the nose 19d will serve as a stop for the clip 8, determining the extent to which the vessel can shift the clip 8 rearwardly with respect to the jaws 3 and 5.

It will be remembered that during the clip clamping operation, the pusher 6 automatically returns to its retracted position to pick up the next clip 8. After several ligating procedures, the forwardmost end of the pusher 6 may become coated with blood, serum or other body fluids which tend to be tacky. As a result of this, in the absence of stop 17, it would be possible for the clip base portion 9 to become adhered to the free notched end 12 of pusher 6 and carried back into the body of the instrument. However, since the nose 19d of stop 17 is permitted to achieve a position behind the base portion 9 of clip 8 (as shown in FIG. 13), the stop nose 19d will ensure that the clip 8 will separate from the notched free end 12 of pusher 6 during return of pusher 6 to its retracted position.

As is indicated above, the jaw 5 is provided with a perforation 28 into which the rounded portion 19d of the hook-shaped end 19a of the short stop leg 19 extends. When the jaws close to clamp a clip, the short leg 19 is received in the perforation 28, permitting the jaws to close.

Modifications may be made in the invention without departing from the spirit of it.

What is claimed is:

1. A surgical instrument for applying hemostatic clips to vessels within a patient, comprising: first and second jaws having opposed clamping surfaces for clamping said clips to a vessel; means for actuating said jaws between a first normal open position and a second clip-clamping position; means for storing a plurality of said clips within said instrument; means for transferring said clips one at a time to said jaws from said storage means; and stop means located totally within said clamping jaws for allowing a clip to be transferred from said storage means to said clamping jaws while preventing said clip from moving toward said storage means during the operation of said actuating means.

2. The instrument of claim 1, wherein said actuating means comprises a pair of handles for shifting said jaws between said first normal position and said second clip-clamping position.

3. The instrument of claim 1, wherein said transfer means comprises a pusher having a free forward end to engage and move said clips from said storage means to a position between said clamping surfaces of said first and second jaws.

4. The instrument of claim 3, wherein said stop means comprises a resilient member having a long leg and a short leg, with said long leg being mounted in a longitudinal depression within said clamping surface of said first jaw, said short leg extending between said opposing clamping surfaces of said jaws, being receivable within a perforation in said second jaw, and having an intermediate clip-contacting nose portion extending between said jaws just behind said forwardmost position of said clip between said jaws.

5. The instrument of claim 4, wherein said nose portion is shiftable between a retracted position within said jaws by a clip being advanced by said pusher and a normal position behind a clip fully advanced to its forwardmost position whereby said nose portion prevents rearward movement of said clip during operation of said actuating means.

6. The instrument of claim 5, wherein each of said clips comprises a V-shaped base terminating in leg members, said V-shaped base of said clip cooperating with said nose portion of said stop means to shift said nose portion to said retracted position as said clip is shifted past said nose portion by said pusher.

7. The instrument of claim 5, wherein said long leg of said stop means is configured so as to bias said nose portion to said normal position.

8. A clip stop for use in a surgical instrument containing a pair of clip-clamping jaws for applying hemostatic clips to vessels within a living body, said clip stop comprising resilient means mounted within one of said jaws and being shiftable totally within said jaws from a normal position to a retracted position by a clip, as said clip is moved to a forward clip-clamping position between said jaws, said resilient means returning to said normal position when said clip is in said forward clip-clamping position, said normal position preventing rearward motion of said clip during the clip-clamping operation.

9. The clip stop of claim 8, wherein said resilient means comprises a substantially L-shaped member having a long leg and a short leg, said long leg being mounted in a longitudinal depression within the clamping surface of one of said jaws, said short leg, extending between the clamping surfaces of said jaws, being receivable within a perforation in the other of said jaws and having an intermediate clip-contacting nose portion extending between said jaws just behind said forward position of said clip to be clamped.

10. The clip stop of claim 9, wherein said short leg contains an intermediate portion of V-shaped configuration having an apex which forms said nose portion.

11. The clip stop of claim 9, wherein said long leg has a free end terminating in a portion lying at an angle to the remainder of said long leg, which portion extends into a perforation at the rearward end of said depression, said long leg being configured so as to bias said clip stop to said normal position.

12. A clip stop for a surgical ligator for applying clamping clips to vessels in a patient's body, said ligator being of the type having first and second jaws having opposed clamping surfaces, a pair of handles to actuate said jaws between open and closed clip-clamping positions, a magazine of ligating clips, a pusher track extending along said opposed jaw surfaces to the forward ends of said first and second jaws, a pusher having a free forward end to engage and transfer said clips singly along said pusher track from said magazine to a forward position between said jaws and a stop to prevent rearward movement of said clip in said pusher track when said clip is applied and clamped to a vessel, said stop comprising a substantially L-shaped resilient member having a long leg and a short leg, said long stop leg being mounted in a longitudinal depression in said clamping surface of said first jaw and being affixed near its free end to said first jaw, said short stop leg extending between said opposed clamping surfaces of said first and second jaws and being receivable in a perforation in said second jaw when said jaws are in said closed clip-clamping position, said short stop leg having an intermediate clip-contacting nose portion normally extending across said pusher track just behind said forward position of said clip between said jaws, said nose portion of said stop being shiftable to a retracted position out of said pusher track by an advancing clip, whereby said nose portion prevents rearward movement of said clip during the clip-applying and clamping operation and assures separation of said clip from said free forward end of said pusher if adhered thereto by body fluids.

13. The structure claimed in claim 12, wherein said stop is made of resilient wire, said short leg thereof having an intermediate portion of V-shaped configuration, said V-shaped configuration having an apex comprising said nose.

14. The structure claimed in claim 13, wherein said long stop leg has a free end terminating in a portion lying at an angle of 90° to the remainder of said long leg, said last mentioned portion extending into a perforation at the rearward end of said depression, a circular bore intersecting said depression near said rearward end thereof, a slotted cylindrical plug located in said bore, said plug affixing said long leg to said first jaw with said long leg extending through said plug slot, said long leg being so configured as to bias said stop nose to its normal position extending across said pusher track.

15. The structure claimed in claim 14, wherein each of said clips comprises a V-shaped base terminating in leg members, said V-shaped base of said clip cooperating with said V-shaped nose of said stop to shift said nose to said retracted position as said clip is shifted past said nose by said pusher.

16. The structure claimed in claim 12, wherein said pusher comprises a side facing said nose portion of said stop when said nose portion is in said retracted position, said pusher side having a longitudinal notch formed therein adjacent said free end of said pusher so sized as to permit said nose portion to partially return to its normal position behind a fully advanced clip.

17. The structure claimed in claim 16, wherein said pusher has a C-shaped cross-section comprising relatively thick longitudinal edge portions joined by a relatively thin longitudinal intermediate portion, said free forward end of said pusher having a thickness equivalent to that of said longitudinal edge portions, said longitudinal notch being formed in said free forward end, said free forward end at said notch having a thickness approximately that of said longitudinal intermediate portion.

* * * * *